(12) United States Patent
Okazawa

(10) Patent No.: US 7,951,928 B2
(45) Date of Patent: May 31, 2011

(54) GENE ENCODING A PROTEIN AND PREVENTIVE/REMEDY FOR NEURODEGENERATIVE DISEASES SUCH AS POLYGLUTAMINE DISEASES BY UTILIZING THE SAME

(75) Inventor: Hitoshi Okazawa, Kanagawa (JP)

(73) Assignee: Tokyo Medical and Dental University, Tokyo (JP)

( * ) Notice: Subject to any disclaimer, the term of this patent is extended or adjusted under 35 U.S.C. 154(b) by 606 days.

(21) Appl. No.: 11/791,053

(22) PCT Filed: Nov. 16, 2005

(86) PCT No.: PCT/JP2005/021041
§ 371 (c)(1),
(2), (4) Date: Oct. 15, 2007

(87) PCT Pub. No.: WO2006/054600
PCT Pub. Date: May 26, 2006

(65) Prior Publication Data
US 2008/0188408 A1     Aug. 7, 2008

(30) Foreign Application Priority Data
Nov. 18, 2004   (JP) ................................. 2004-335065

(51) Int. Cl.
C07H 21/04     (2006.01)
C12P 21/06     (2006.01)
C12N 15/74     (2006.01)
C12N 5/02      (2006.01)

(52) U.S. Cl. ................... 536/23.5; 435/69.1; 435/320.1; 435/325

(58) Field of Classification Search .......................... None
See application file for complete search history.

(56) References Cited

U.S. PATENT DOCUMENTS

| 6,022,740 A * | 2/2000 | Sudol et al. ................... 435/325 |
| 6,495,376 B1 | 12/2002 | Lu et al. |
| 2003/0119009 A1 * | 6/2003 | Stuart et al. ........................ 435/6 |

FOREIGN PATENT DOCUMENTS

| JP | 2002-541065 | 12/2002 |
| WO | 00/48621 | 8/2000 |

OTHER PUBLICATIONS

Sudol, M., et al., Characterization of the Mammalian YAP (Yes-associated Protein) Gene and Its Role in Defining a Novel Protein Module, the WW Domain, J. Biol. Chem., vol. 270, No. 24, Jun. 16, 1995, p. 14733-14741.

Vassilev, A, et al., TEAD/TEF transcription factors utilize the activation domain of YAP65, a Src/Yes-associated protein localized in the cytoplasm, Genes Dev., May 15, 2001, vol. 15, No. 10, p. 1229-1241.

Basu, S., et al., Akt Phosphorylates the Yes-Associated Protein, YAP, to Induce Interaction with 14-3-3 and Attenuation of p73-Mediated Apoptosis, Mol. Cell, Jan. 2003, vol. 11, No. 1, p. 11-23.

Hoshino, M., et al., General transcriptional repression by polyglutamine disease proteins is not directly linked to the presence of inclusion bodies, Biochem. Biophys. Res. Commun., Jan. 2, 2004,vol. 313, No. 1, p. 110-116.

Okazawa, H., Polyglutamine diseases: a transcription disorder?, Cell. Mol. Life Sci, Jul. 2003, vol. 60, No. 7, p. 1427-1439.

McCampbell, A., et al., Histone deacetylase inhibitors reduce polyglutamine toxicity, Proc. Natl. Acad. Sci. USA, Dec. 18, 2001, vol. 98, No. 26, p. 15179-15184.

Igarashi, S., et al., Search for polyglutamine disease genes by candidate gene approach, Protein, Nucleic acid and Enzyme, Dec. 10, 2001, vol. 46, No. 16, p. 2295-2298.

Hoshino, M., et al., Gene expression profile change by transcriptional suppression in primary culture neurons: a model of polyglutamine diseases, Bulletin of the Japanese Society for Neurochemistry, Aug. 10, 2004, vol. 43, No. 2/3, p. 542.

Hoshino, M., et al., Changes in gene expression following transcriptional suppression by alpha-amanitin treatment of primary culture neurons: A model of polyglutamine diseases, Neuropathology, Jun. 2005, vol. 25, No. 2, p. A21.

Komuro Akihiko et al, "WW domain-containing protein YAP associates with ErbB-4 and acts as a co-transcriptional activator for the carboxyl-terminal fragment of ErbB-4 that translocates to the nucleus," The Journal of Biological Chemistry, Aug. 29, 2003, vol. 278, No. 35, pp. 33334-33341.

Yagi, Ryohei et al, "A WW domain-containing Yes-associated protein (YAP) is a novel transcriptional co-activator," The EMBO Journal, May 4, 1999, vol. 18, No. 9, pp. 2551-2562.

Database EMBL, Oct. 8, 2001, "Mus musculus yes-associated protein 1, mRNA (cDNA clone MGC:25351 Image:4239820), complete cds." Retrieved From EBI accession No. EMBL:BC014733.

* cited by examiner

*Primary Examiner* — Lorraine Spector
*Assistant Examiner* — Stacey MacFarlane
(74) *Attorney, Agent, or Firm* — Carmody & Torrance LLP

(57) ABSTRACT

To provide a novel protein that can be a preventive/remedy in neurodegenerative diseases such as polyglutamine diseases based on the finding obtained by revealing the relationship between transcriptional dysfunction and neuronal death. Disclosed is a protein that is one of the following proteins (a) and (b).
(a) A protein including an amino acid sequence represented by any one of SEQ ID NOS: 1 to 3.
(b) A protein including an amino acid sequence in which one to several amino acids are deleted, substituted or added in the amino acid sequence of (a), the protein having a dominant negative effect on a transcriptional activation factor YAP.

5 Claims, No Drawings

GENE ENCODING A PROTEIN AND PREVENTIVE/REMEDY FOR NEURODEGENERATIVE DISEASES SUCH AS POLYGLUTAMINE DISEASES BY UTILIZING THE SAME

CROSS REFERENCE TO RELATED APPLICATIONS

This application is a National Stage application of International Application No. PCT/JP2005/021041, filed Nov. 16, 2005.

This application incorporates by reference the material contained on the compact disc submitted herewith. The disc contains the file entitled N-MD002-07P—Sequence Listing, which was created on May 11, 2007.

TECHNICAL FIELD

The present invention relates to a novel protein and a gene that encodes it. More specifically, the present invention belongs to the technical field of preventive/remedy for neurodegenerative diseases such as polyglutamine diseases.

BACKGROUND ART

Transcriptional dysfunction is an important pathologic factor associated in neurodegenerative diseases such as polyglutamine diseases. The present inventors have proved that polyglutamine diseases involve reduction of entire gene expression rather than reduction of expression of several particular genes (see, Non-Patent Literature 1). That is, a large number of transcription factors are known to co-localize or interact with mutant proteins that lead to polyglutamine diseases. A general transcription level, equivalent to an overall function level of transcription factors, is down-regulated by mutant polyglutamine protein. One of the major challenges to be tackled for the treatment of polyglutamine diseases is to unravel the relationship between transcriptional dysfunction and neuronal death. However, it is not certain whether inhibition of transcription triggers neuronal death. Also, the mechanism by which significant inhibition of transcription causes neuronal death remains totally elusive.

As described above, cellular transcriptional dysfunction is one of the major molecular-level causes of neurodegenerative diseases, particularly polyglutamine diseases. However, it is still unknown whether or not transcriptional dysfunction actually causes neuronal death and in what manner neuronal death occurs.

[Non-Patent Literature 1] BBRC, vol. 313, p110-116 (2004)

DISCLOSURE OF THE INVENTION

Accordingly, an object of the present invention is to reveal the relationship between transcriptional dysfunction and neuronal death and to provide on the basis of the obtained finding a novel protein that can be a preventive/remedy for neurodegenerative diseases such as polyglutamine diseases.

In order to solve the above-described problems, the present inventors investigated neuronal cells interacted with α-amanitin (AMA) that specifically inhibits RNA polymerase II, and found that amanitin caused extremely mild neuronal death. It took 5 days or more before half the population of the neural cells died. Analysis of the neural cells using an electronic microscope indicated that morphological characteristics of the dying cell is distinguished from those seen in apoptosis and necrosis. Moreover, no DNA ladders were observed upon electrophoresis. Furthermore, the dying neuronal cell possessed a vacuole in cytoplasm that is different from that of autophagosome labeled with pEGFP-LC-3.

Comparison of expression of genes associated with apoptosis with expression of genes associated with amanitin-induced neuronal cell death led to the identification of novel isoforms of YAP, which is known as a transcriptional activation factor (coactivator). The novel isoforms are expressed during the course of atypical neuronal death. These isoforms lack a transcriptional activation domain and suppressed apoptosis of MCF-7 cell that is mediated by P73 and YAP. This indicates that the novel isoforms have a dominant negative effect on cellular death. Adenovirus vector expressing YAP isoforms also suppressed neuronal death induced by a-amanitin. That is, it has been revealed that suppression of transcription causes atypical and mild neuronal death, but cellular death can be suppressed by the novel YAP isoforms.

The process of this mild neuronal death is quite different from those of apoptosis, necrosis, and autophagy. The present inventors propose this novel pattern of neuronal cell death as a prototype of neurodegeneration in polyglutamine diseases and, using this the knowledge, completed the present invention.

That is, the present invention includes the following (1) to (6).

(1) A protein that is one of the following proteins (a) and (b):
   (a) a protein including an amino acid sequence represented by any one of SEQ ID NOS: 1 to 3; and
   (b) a protein including an amino acid sequence in which one to several amino acids are deleted, substituted or added in the amino acid sequence of (a) having an amino acid sequence represented by SEQ ID NO: 4as a partial amino acid sequence thereof and having a dominant negative effect exerted on a transcriptional activation factor YAP.

(2) A gene encoding the protein according to (1).

(3) A recombinant vector including the gene according to (2).

(4) A transformant including a recombinant vector containing the gene according to (2).

(5) A preventive/remedy for a neurodegenerative disease such as a polyglutamine diseases, spinocerebellar degeneration, amyotrophic lateral sclerosis, Alzheimer's disease, and Parkinson's disease, wherein the preventive/remedy includes the protein according to (1).

(6) A preventive/remedy for a neurodegenerative disease such as a polyglutamine diseases, spinocerebellar degeneration, amyotrophic lateral sclerosis, Alzheimer's disease, and Parkinson's disease, wherein intercellular signal transduction mediated by the protein according to (1) is utilized.

According to the present invention, a novel neuronal death pattern (omega process, OP) that progresses extremely slowly and novel YAP isoforms that lack a transcriptional activation domain have been identified, and it has been proved that these isoform play an important role in inhibiting OP.

The novel YAP isoforms suppress neuronal death and therefore, can be utilized as a preventive/remedy for neurodegenerative diseases such as polyglutamine diseases.

BEST MODE FOR CARRYING OUT THE INVENTION

The present invention will now be described in detail. First, the present inventors prepared many different types of siRNAs against RNA polymerase II (PolII) in order to. reveal the relationship between transcription function and neuronal death, but attempts to sufficiently inhibit PolII using siRNA failed, as did recent research that focuses on elucidating the fundamental transcription mechanism by a similar approach. Accordingly, we utilized α-amanitin, an effective inhibitor against PolII. This AMA molecular can bind PolII.

First, solutions containing three different concentrations of AMA were added to culture media of Hela cells, primary cultured cortical neurons of rat embryo (E15), and primary cultured cerebellar neurons of rat. Subsequent measurement of uptake of BrU showed that AMA suppressed transcription in the cortical neurons and cerebellar neurons. The proportions of the liviving cells in the population of the AMA-treated neurons and Hela cells were calculated, leading to the discovery that AMA induces progressive cellular death. The AMA-induced cellular death was significant particularly in the primary cultured neurons and their half-life period was five days or more—the primary cultured neurons died obviously earlier than those that had not been treated with AMA. Moreover, the cellular death rate was dependent on AMA concentration. In this AMA-induced cellular death, neuronal cell death progressed very slowly as compared with low-potassium-induced apoptosis of cerebellar neurons.

Primary morphologic change of the Hela cells started in 6 hours to 12 hours after the addition of AMA, resulting the generation of cytoplasmic vacuoles around the nucleus. Similar vacuoles, although in small proportion, were also observed in the cortical neurons after two days from the AMA treatment. Immunohistochemical analysis using specific antibodies against organelles revealed that these vacuoles were not originated from any of mitochondria, Golgi body, lysosome and endosome. Also, the vacuoles were not originated from autophagosome because EGFP-LC3, a marker protein for phagosome, was not localized in the vacuoles. The use of ECFP-ER, an enhanced cyan fluorecent protein having at 5' end a sequence targeting ER (one of the organelles) and at 3' end a KDEL sequence searching for ER, revealed that the vacuoles were swollen ERs, suggesting that AMA put stress on ER.

The cortical neurons and Hela cells were observed using an electron microscope, and no apoptosis- or necrosis-related phenomena, such as aggregation of chromosome, enlargement of mitochondria and expansion of cytoplasm, were observed. Even in genome DNA analysis of the cell line and primary neurons, no DNA ladders were observed as a result of AMA treatment.

It was established from these experiments that AMA causes mild neuronal cell death that occurs through a pathway that is different from those of apoptosis, necrosis and autophagy. The present inventor has termed this new neuronal death as "omega process, OP."

Next, in order to clarify the molecular mechanism underlying the OP (omega process), we performed microarray analysis. Expression of genes associated with AMA-induced cellular death of cortical neurons and cerebellar neurons and expression of genes associated with low-potassium-induced apoptosis of cerebellar neuron were compared. Experiment was performed twice for each type of cellular death. This microarray analysis led to the identification of 8 genes that offered different expression levels both in apoptosis and OP, and 11 genes that offered different expression levels specifically in OP. The latter set of genes contained YAP, a transcriptional activation factor (coactivator) which is known to play a key role in p73-mediated apoptosis. It was confirmed by Northern blotting that AMA down-regulated YAP expression in a transcription stage.

PCR cloning of RNAs obtained from the cortical neurons and cerebellar neurons led to the identification of novel YAP isoforms. These novel isoforms have additional inserts of 13nt, 25nt and 61nt, respectively. The cortical neuron-derived cDNAs obtained by RT-PCR were amplified and subcloned into pBluescript vector. E. coli cells were then transformed with the pBluescript vector and spread on a dish to grow. Among 14 colonies picked out of the dish, the numbers of colonies derived from the 13nt, 25nt, and 61nt inserts were 10, 1, and 3, respectively. The sequences of these inserts matched their genome sequences, and the resultant introns of the genome had the consensus sequences recognized upon splicing. Before expression of these three different isoforms, reading-frame shift occurred by insertion of additional nucleotides, and therefore, they lacked a transcriptional activation domain that YAP originally has.

Subsequently, RT-PCR was performed to investigate in which tissues the novel YAP isoforms were expressed. Interestingly, isoforms respectively including additional 13nt and 61nt inserts (ins 13 and ins 61) were relatively specifically expressed in neurons. In the analysis of cerebral tissues containing a large number of glial cells and cells other than neural cells, only a faint band of ins 13 was observed on the gel. The expression of ins 61 was very specific to cortical neurons. In kidney lane, a band was observed that was larger in size than the ins61 band. No ins25 was detected by RT-PCR.

The present inventors speculated that the YAP isoforms lacking the transcriptional activation domain result in opposite effect in neuronal death; as expected, the molecules lacking that domain offered a dominant negative effect on cisplatin-induced apoptosis of MCF-7 cells. At the same time, it was confirmed that the cells transformed with the cDNAs expressed those isoforms. The novel isoforms were investigated whether they suppress OP. After 4 days from the addition of AMA, the expression of the novel isoforms reduced cellular death rate both in cortical neurons and cerebellar neurons.

In order to investigate whether p73 and YAP mediate OP as they do cisplatin-induced apoptosis of MCF-7 cells, siRNAs for P73 and YAP were added to Hela cells and cortical neurons. In Hela cells the addition of either of these siRNAs inhibited OP. This supports hypothesis that OP is also mediated by a cascade of YAP and p73.

Finally, temporal changes of YAP isoforms during the course of OP were observed by Western blotting. Interestingly, the levels of the novel isoforms were stable for a relatively long period in cortical neurons although the level of rYAP (=hYAP2) began to decrease after 3 days from the experiment. The levels of the novel YAP isoforms in cortical neurons were large compared with those in Hela cells. Similar expression level changes were also seen in cerebellar neurons. The net result of this is that novel YAP isoforms specific to neurons suppress neuronal cell death by a dominant negative effect on YAP. One of the major questions in neurodegeneration has been that neuronal cell death progresses at a low rate; the finding that these novel isoforms offering a dominant negative effect are expressed specifically in neurons, however, well explains this question.

As explained above, a novel prototype of cellular death called "OP" was discovered that explains why neurodegeneration progresses extremely slowly. Moreover, it has been proved that novel YAP isoforms that lack the transcriptional activation domain play an important role in inhibiting OP. Microarray analysis showed that expression levels of analogous molecules changed both in apoptosis and OP. Accordingly, there is a possibility that OP partially shares some molecular mechanisms with apoptosis. These two types of cellular death are triggered by different molecules that are specific to different cellular death processes. However, there is a possibility that the molecules are the same.

Accordingly, the above-described novel isoforms of YAP can be utilized as a preventive/remedy for neurodegenerative diseases such as polyglutamine diseases, leading to a novel method for the treatment of neurodegenerative diseases.

Such novel YAP isoforms lacking the transcriptional activation domain as described above are composed of any one of amino acid sequences represented by SEQ ID NOS: 1 to 3. These proteins can be obtained from any protein derived from human or animal or from any synthesized protein, all of which contain an amino acid sequence that is identical or substantially identical to the amino acid sequences of SEQ ID NOS: 1 to 3.

As used herein, the protein having the substantially identical amino acid sequence refers to any protein that is composed of an amino acid sequence in which one to several amino acids are deleted, substituted or added in any one of the amino acid sequences of SEQ ID NOS: 1 to 3 and having an amino acid sequence represented by SEQ ID NO: 4 as a partial amino acid sequence thereof and that has a dominant negative effect on the transcriptional activation factor YAP. Moreover, it is preferable that the protein be about 90% or more, more preferably, about 95% or more homologous to any one of the amino acid sequences represented by SEQ ID NOS: 1 to 3.

Moreover, the C-terminal of the protein of the present invention may be any of a carboxyl group, a carboxylate, an amide, and an ester, and the amino group of the N-terminal of the amino acid residue may be capped by a protective group such as formyl group or acetyl group. Furthermore, the protein of the present invention may be a complex protein such as a so-called glycoprotein in which sugar chains are combined, or a salt with a physiologically acceptable acid or base.

The protein of the present invention can be produced by any known process for purifying protein from human or animal cells or tissues. Moreover, the protein of the present invention can be produced from cultured transformants containing a gene encoding that protein. Alternatively, the protein may be produced according to a known method of peptide synthesis. Examples of synthesizing methods are a solid-phase synthesizing method, a liquid-phase synthesizing method, and so forth. More specifically, the protein of interest can be prepared in the following manner: Some peptides or amino acids that can potentially constitute the protein of the present invention are condensed together and, where the product contain protective groups, the protective groups are cleaved off the product.

When the protein is to be prepared from transformants, any general method can be adopted: The gene encoding the protein is ligated into a suitable expression vector, a host organism is transformed with the vector to produce transformants, and the transformants are cultured under a predetermined condition followed by recovery of the target protein.

The gene encoding the protein (i.e., the novel YAP isoform) of the present invention may be any one which has a predetermined nucleotide sequence. Specifically, any of genomic DNA, cDNA derived from cells or tissues and synthetic DNA can be used.

Upon insertion of gene into a vector, for example, a method can be used that includes cleaving off a purified gene by digestion with an appropriate restriction enzyme and inserting the gene into an appropriate vector DNA at a particular restriction site or multiple cloning site, ligating the gene to the vector. In addition to the gene according to the present invention, the expression vector may further incorporate for instance a promoter, a terminator, and/or a ribosome-binding sequence.

For the vector, there can be used plasmids derived from *E. coli*; plasmids derived from *Bacillus subtilis*; plasmids derived from yeast, bacteriophage such as λ-phage; retroviruses such as Moloney leukemia virus; animal viruses such as vaccinia virus and baculovirus; and so forth.

Transformation of a host organism with the above-described expression vector results in the production of desired transformants. The host organism is not particularly limited as long as it is capable of expressing the gene of the present invention; for example, *Escherichia bacterium* such as *Escherichia coli*, Bacillus bacterium, yeast, animal cell, and so forth can be used. Examples of applicable transformation methods include, but not limited to, known techniques such as calcium-chloride method and electropolation.

By culturing this transformant, the protein of the present invention can be produced. Upon recovery of the protein, the cells are crushed according to need and are removed by centrifugation or the like. Thereafter, general biochemical methods used for protein purification, such as, ammonium sulfate precipitation, gel chromatography, ion-exchange chromatography, and affinity chromatography, are used singly or where necessary in combination for the purification of the protein.

In cases where the protein (a novel YAP isoform) is used as a preventive/remedy for neurodegenerative diseases such as polyglutamine diseases, it is administered parenterally (e.g., intravenously). When it is to be used in the form of injectable solutions, the protein can be formulated into a therapeutic agent using a suitable pharmacologically acceptable carrier such as salt solution, glucose solution, or a mixture of saline solution and glucose solution. In addition, problems may arise in vivo drug delivery as to whether or not the agent can pass through the blood-brain barrier. If the blood-brain barrier offered poor permeability to the agent, a method can be appropriately used that includes the step of adding HIV-derived TAT amino acid sequences to the agent to allow it pass through the agent through blood-brain barrier, for example.

When the gene encoding the novel isoform is used as a preventive/remedy, the gene may be incorporated into the expression vector so that the novel isoform is expressed in target cells after administration. TAT sequences may be added so that the expressed protein can be introduced into neuronal cells. Moreover, the vector into which the gene is incorporated may be encapsulated in appropriate capsid protein, liposome, virus particle or the like. This allows the gene to be specifically delivered to a target cell or tissue, where the novel YAP isform(s) are expressed.

Furthermore, another form of a preventive/remedy for neurodegenerative diseases is to utilize intracellular signal transduction mediated the novel YAP isoform. Akt, for example, is a serine threonine kinase, a protein also called as protein kinase B (PKB). This modifies or phosphorylates YAP in the course of intracellular signal transduction. YAP is phosphorylated and thereby a binding site for 14-3-3 protein is formed. Suppression of YAP degradation by inhibiting phosphatase can enhance the effect of preventing neuronal death. Alternatively, agents for inhibiting c-Abl and/or ATM which activate YAP and agents for inhibiting p73 and/or p53 which bind to and act on YAP can be used as the preventive/remedy for neurodegenerative diseases.

EXAMPLES

Hereinafter, experimental techniques in the present invention will be explained in detail.

(Primary Culture of Neuronal Cells)

A cerebral cortical tissue segregated from E17 Wistar rat embryo and a cerebellar tissue segregated from P7 Wistar rat novelborn were shredded with a razor, and treated with a phosphate buffered saline (hereinafter referred to as "PBS"; pH 7.5) containing 0.25% trypsin (Gibco) at 37° C. for 20 min, with gentle shaking every 5 min. Subsequently, the reaction was quenched by replacing the PBS with DMEM containing a 50% fetal bovine serum (hereinafter referred to as "FBS"), and DNaseI (Boehringer Mannheim) was added to a final concentration of 100 μg/ml. The tissues were segregated gently by pipetting with a blue tip. The cells were filtrated through a nylon mesh (FALCON, pore size: 70 mm) by centrifuge for precipatation and resuspended in DMEM additionally containing 20 mM glucose, 16 mM sodium hydrogen carbonate, 4 mM glutamine, 25 μg/ml gentamicin and 10% FBS. The suspension was added into a polylysine-coated 24-well plate (Corning) and the cells were cultured so that each well has $3\times10^5$ cells. After 12 hours, cytosine arabinoside was added to the culture wells to a final concentration of 4M in order to prevent glial cell proliferation. To induce OP, α-amanitin (Sigma) was then added to the culture wells to a final concentration of 10 μg/ml or 25 μg/ml except for wells for concentration dependency experiment, and α-amanitin was added to the wells for concentration dependency experiment to final concentrations ranging from 10 μg/ml to 250 μg/ml.

(Cellular Death Assay)

The cells were treated for 5 min with 0.4% Trypan Blue solution (Invitrogen). In each experiment, 10-20 spots were randomly selected from each of the three dishes at 100× magnification. In these spots the numbers of blue-stained cells (dead cells) and non-stained cells (living cells) were counted to a total of at least 2,000.

(Electron Microscope Observation)

The cells were washed 3 times with PBS, fixed with 2.5% glutaraldehyde/ 0.1M PB, and further fixed with 1% $OSO_4$/ 0.1M PB for 2 hours. The fixed cells were dehydrated through an ethanol gradient and embedded in epoxy resin. Then, the ultra-thin cell slice was stained with uranyl acetate and lead citrate, and observed using HITACHI H-7000 Electron Microscope.

(Identification of Amanitin-Induced Vacuoles)

Hela cells were treated with a-amanitin (Sigma) for 6 hours, washed with PBS, and fixed with 4% paraformaldehyde at room temperature for 15 min. Subsequently, the cells were reacted with the following primary antibodies for 1 hour at room temperature: mouse anti-CCO1 monoclonal antibody (1:1000 dilution; Molecular Probes), mouse anti-EEA1 monoclonal antibody (1:100 dilution; Transduction Lab.), rabbit anti-calnexin polyclonal antibody (1:100 dilution; Stressgen), mouse anti-golgi 58k monoclonal antibody (1:100 dilution; Sigma), and anti-CD63 (1:100 dilution; Cymbus Biotechnology Ltd.). Then, the cells were then visualized by reaction with Alexa fluor 488 (1:10000 dilution; Molecular Probes) as the secondary antibody at room temperature for 30 min, placing them in a condition ready for detection by immunostaining. Thereafter, pEGFP-LC3 or pEGFP-ER (BD Biosciences) was transfected with the Hela cells using Superfect (Qiagen) in accordance with the manufacturer procedure.

(RNA Probe for Microarray Analysis)

The cells were washed twice with PBS and treated with TRIZOL reagent (INVITROGEN) in a culture dish, followed by extraction of total RNA in accordance with the product procedure. The RNA was labeled and amplified using Agilent Fluorescent Linear Amplification Kit (Agilent technologies: G2554A) in accordance with the manufacturer procedure. First, double-stranded cDNA containing T7 promoter was synthesized from 2 μg of the total RNA using MMLV reverse transcriptase, oligo dT primer containing T7 promoter sequence, and random hexamer (40° C., 4 hours). Using the resultant cDNA as a template and using Cy3- or Cy5-labeled CTP, cRNA was synthesized by reaction with T7 RNA polymerase. cRNAs were prepared from cortical neurons treated with AMA, cerebellar neurons treated with AMA and cerebellar neurons treated with low potassium, and labeled with either Cy3 or Cy5. The synthesized cRNAs were precipitated with lithium chloride, washed with ethanol, and dissolved in nuclease free-water. To check the cRNAs for integrity, measurements of optical density were conducted at $OD_{250}$, $OD_{280}$, $A_{552}$ (for Cy3), and $A_{650}$ (for Cy5). Then, the $OD_{260}$/$OD_{280}$, amplification rate, and pigment content [pmol/μg RNA] of each cRNA was determined. The cRNA samples were of high quality in terms of these parameters: ($OD_{260}$/$OD_{280}$:2.0<, amplification rate: 400<, Cy3 content: 15<[pmol/μg RNA], and Cy5 content: 12<[pmol/μg RNA]).

(Microarray Analysis)

For hybridization, in situ hybridization kit plus (Agilent technologies: 5184-3568) was used in accordance with the manufacturer procedure. Firstly, cRNA samples labeled with Cy3 or Cy5 (each weighs 1 μg) were mixed and treated with a fragmentation buffer at 60° C. for 30 min. The fragmented cRNA was reacted at 60° C. for 17 hours with Mouse Development Oligo Microarray (Agilent technologies: G4120A) containing 20,371 60-bp oligonucleotides of mouse cDNA. Then, the reacted microarray was washed twice, and dried by blowing nitrogen gas (99.999%) thereto using an air gun (Nihon mycrolis KK) equipped with a filter.

Fluorescent signals were detected by CRBIO IIe (Hitachi software engineering Co., Ltd.), a microarray scanner. The data was analyzed on DNASIS array (Hitachi software engineering Co., Ltd.), an analysis software. Fluorescent signals from control spots and those spots emitting too intense fluorescence due to abnormal signal were excluded in data analysis. The signal intensity of each spot was standardized with respect to the total signal intensity. The standardized signal intensities were plotted on a scattering diagram, with Cy3 fluorescence-derived intensity on Y axis and Cy5 fluorescence-derived intensity on X axis. The fluorescence ratio of Cy3 to Cy5 was calculated, and genes with a Cy3/Cy5 value ranging from 2.0 to 0.5 were tabularized.

(PCR Cloning)

RNA La PCR Kit (AMV)(Takara) was used for RT-PCR cloning of YAP by using cDNA obtained by reverse transcription of 1 μg of total RNA of rat cortical neuron and by using two primers-F: 5'-GGAATTCTATGGAGCCCGCGCAA-3' having a nucleotide sequence represented by SEQ ID NO: 5 and R: 5'-ACGCGTCGACCTATAACCACGTGAG-3' having a nucleotide sequence represented by SEQ ID NO: 6. PCR was performed for 35 cycles under the following conditions for cDNA amplification: 94° C. for 30 sec, 52° C. for 30 min, and 72° C. for 90 sec. The PCR product, cDNA, was inserted into pBluescriptII SK+using EcoRI and SalI. The amplified cDNA was sequenced on ABI PRISM™ 310 DNA Sequencer (Applied Biosystems) using ABI PRISMTM BigDye™ Terminator Cycle Sequencing Kit ver.3.1 (Applied Biosystems), where primers in which the sequences of both M13 and a segment of the synthesized cDNA are contained in combination with were used. The pBluescript vectors containing 13nt, 25nt, and 61nt YAP inserts were termed pBSins13, pBSins25 and pBSins61, respectively. The above-described YAP inserts were ligated into pCI-neo vectors (Promega), and these three vectors were termed pCIins13, pCIins25 and pCIins61, respectively.

(Western Blotting Analysis)

All of the cells were dissolved on their culture dishes in solution containing 62.5 mM tris-HCl (pH 6.8), 2% (w/v) SDS, 2.5% (v/v) 2-mercaptoethanol, 5% (w/v) glycerine and 0.0025% (w/v) bromphenol blue. The concentrations of the cell-dissolved solutions were so adjusted that on an SDS-PAGE gel $3.3 \times 10^4$ Hela cells were present per one lane and $1.0 \times 10^5$ primary cultured neurons were present per one lane. The samples were then run on the gel, transferred onto a polyvinylidene difluoride film (PVDF: Fine Trap, Nihon Eido), and treated with corresponding primary antibody for 1 hour, treated for a further 30 min with the secondary antibody labeled with horseradish peroxidase, and visualized by ECL Western Blotting Detection System (Amersham Bioscinces). Dilution ratios of the primary and secondary antibodies are as follows: rabbit anti-YAP polyclonal antibody (H-125, Santa Cruz)=1:1000, mouse anti-GAPDH monoclonal antibody (Chemicon)=1:100000, HRP-labeled anti-mouse-IgG (Amersham)=1:5000, and HRP-labeled anti-rabbit-IgG (Amersham)=1:3000.

(Adenovirus Vector)

As the adenovirus vector lacking replication competence, Adenovirus Expression Vector Kit (TAKARA SHUZO CO., LTD.) was used in accordance with the manufacturer procedure. The cDNAs of YAP was cleaved from pBSins13, pBSins25 and pBSins61 by digestion with EcoRI and SalI. Both ends of each of the cDNA fragments were blunted using Blunting high kit (Toyobo CO., LTD.), and the fragments were inserted into pAxCAwt cosmid (Takara) using SwaI. The purified cosmid was introduced into 293 cells together with adenovirus DNA by calcium phosphate method, and the culture solution of dead cells was collected as virus solution. After several amplifications, the clonality ($5 \times 10^8$ to $5 \times 10^9$ PFU/ml) of this vector was investigated by using endonuclease and PCR. Aadenovirus vectors AxCAins13, AxCAins25, and AxCAins61 were produced. Hela cells and primary cultured neurons were infected with these vectors at multiplicity of infection (MOI) of 100. Moreover, preliminarily, protein expression efficiency and toxicity of adenovirus were investigated by infecting primary cultured neurons with an EGFP-incorporated vector and mock vectors with various MOIs. At MOI of 100, 90% or more of neurons expressed EGFP. The difference of proportions of dead cells between non-infected neurons and mock-infected neurons was investigated by using Trypan Blue; the difference was as low as about 3% even at MOI of 500 or more.

(Northern Blotting)

Ten micrograms of total RNA extracted from the primary cultured neurons was electrophoresed on a MOPS/formaldehyde gel. The separated RNA fragments were transferred and immobilized to Hybond-N (Pharmacia) by UV cross-linking (exposure dose=120,000 $\mu J/cm^2$). The full-length cDNA with the 61nt insert was cleaved from pBSins61 and purified by passing it through a gel and labeled with [a32P]dCTP (Amersham) using Random Primer DNA-labeling kit (Takara). The probes labeled with 32P were reacted with a nylon film at 60° C. and allowed to stand overnight for permeation. The reacted film was washed twice with 1×SSC containing 0.1% SDS at 50° C. for 20 min, and washed twice with 0.1×SSC containing 0.1% at 60° C. for 20 min. The film was exposed to X-ray film at −80° C. for an appropriate time.

(RNA Interference)

The cells were transfected with siRNA oligonucleotides using RNAiFect (QIAGEN) in accordance with the manufacturer procedure: After 24 hours from inoculation, $2.5 \times 10^4$ cells, contained in each of the 6 wells of a plate, were infected with 0.5 μg of siRNA. After 24 hours from infection, AMA was added to each well to a final concentration of 10 μg/ml. Furthermore, after 24 hours, cellular death assay was performed. The same sequences of siRNAs for YAP and p73 as previously disclosed ones were used

INDUSTRIAL APPLICABILITY

The new protein of the present invention and the preventive therapeutic agent of the present invention using that protein for neurodegenerative diseases such as polyglutamine diseases can be used for preventive/remedy against neurodegenerative diseases such as polyglutamine diseases, spinocerebellar degeneration, amyotrophic lateral sclerosis, Alzheimer's disease, and Parkinson's disease.

The invention claimed is:

1. A purified nucleic acid encoding a protein that is one of the following proteins (a) and (b):
    (a) A protein comprising an amino acid sequence represented by SEQ ID NO: 3; and
    (b) A protein comprising an amino acid sequence in which one to several amino acids are deleted, substituted or added in the amino acid sequence of (a), the protein having an amino acid sequence represented by SEQ ID NO: 4 as a partial amino acid sequence thereof and having a dominant negative effect on a transcriptional activation factor YAP.

2. A recombinant vector comprising the nucleic acid according to claim 1.

3. A transformant comprising a recombinant vector containing the nucleic acid according to claim 1.

4. The nucleic acid according to claim 1, wherein the protein comprises the amino acid sequence represented by SEQ ID NO: 3.

5. The nucleic acid according to claim 1, wherein the nucleic acid encodes protein (b) having the amino acid sequence represented by SEQ ID NO: 4 in the carboxyl terminus thereof.

* * * * *